United States Patent [19]
Haczek et al.

[11] Patent Number: 6,102,700
[45] Date of Patent: Aug. 15, 2000

[54] CLEANSING IMPLEMENT AND ELECTRICALLY POWERED DENTAL CLEANSING DEVICE

[75] Inventors: Werner Haczek, Nürnberg; Bernhard Boland, Frankfurt; Peter Hilfinger, Bad Homburg; Armin Schwarz-Hartmann, Albig, all of Germany

[73] Assignee: Braun Aktiengesellschaft, Germany

[21] Appl. No.: 08/381,831

[22] PCT Filed: Jul. 3, 1993

[86] PCT No.: PCT/DE93/00596

§ 371 Date: Jun. 10, 1996

§ 102(e) Date: Jun. 10, 1996

[87] PCT Pub. No.: WO94/04093

PCT Pub. Date: Mar. 3, 1994

[30] Foreign Application Priority Data

Aug. 12, 1992 [DE] Germany ............................ 42 26 659
Mar. 20, 1993 [DE] Germany ............................ 43 09 078

[51] Int. Cl.[7] .................................. A61C 1/07; A61C 3/03; A61C 3/08
[52] U.S. Cl. ............................................................ 433/118
[58] Field of Search ...................................... 433/118, 119, 433/120, 121, 122, 123; 132/321, 322; 601/139

[56] References Cited

U.S. PATENT DOCUMENTS

| 1,083,766 | 1/1914 | Souzon . | |
|---|---|---|---|
| 3,091,033 | 5/1963 | Ellman . | |
| 3,472,045 | 10/1969 | Nelson et al. . | |
| 3,552,022 | 1/1971 | Akelsson . | |
| 3,855,702 | 12/1974 | Malmin | 433/165 |
| 3,987,549 | 10/1976 | Robertelli . | |
| 4,367,759 | 1/1983 | Kline . | |
| 4,576,190 | 3/1986 | Youssef | 132/322 |
| 4,880,382 | 11/1989 | Moret et al. . | |
| 4,922,936 | 5/1990 | Buzzie et al. . | |
| 4,976,625 | 12/1990 | Weissman | 433/118 |
| 5,002,487 | 3/1991 | Tichy | 438/118 |
| 5,573,020 | 11/1996 | Robinson | 132/322 |

FOREIGN PATENT DOCUMENTS

| 0 028 530 | 5/1981 | European Pat. Off. . |
|---|---|---|
| 1 011 116 | 6/1952 | Germany . |
| 1 766 651 | 5/1968 | Germany . |
| 258 566 A1 | 1/1986 | Germany . |
| 88 09 217 U | 7/1988 | Germany . |
| 40 05 625 | 2/1990 | Germany . |
| 90 14 271 U | 10/1990 | Germany . |

Primary Examiner—Nicholas D. Lucchesi
Attorney, Agent, or Firm—Fish & Richardson P.C.

[57] ABSTRACT

The invention is directed to an electrically powered dental cleansing device (1) to which a cleansing implement (32) is fitted. In this manner, the cleansing implement (32) can be rotated about its longitudinal axis. The cleansing implement (32) is configured as an integrally formed part comprising a thin and elongate cleansing shaft (125). The cleansing shaft has at least one longitudinal edge and is provided with a plurality of serrations.

38 Claims, 8 Drawing Sheets

CLEANSING IMPLEMENT AND ELECTRICALLY POWERED DENTAL CLEANSING DEVICE

This invention relates to an electrically powered dental cleansing device comprising a cleansing implement which is rotatable about its longitudinal axis by a motor provided in the dental cleansing device.

Such a dental cleansing device and a cleansing implement are known from German Patent No. 1,011,116. This patent discloses a pencil mounted on a shaft coupled to a drive unit. The pencil is comprised of a plurality of individual hairs of a length dimensioned such that the pencil is tapered towards a pointed free end. By means of the drive unit, the pencil can be rotated about its longitudinal axis for performing a tooth cleaning function. However, because of the relatively large dimensions of the pencil, this implement is not suitable for interproximal cleaning.

From DE-OS 1,766,651 a device is known which can be used by dentists for grinding off amalgam fillings, for example. For tooth treatment, the device comprises an instrument similar to a blade which can be caused to perform a lifting motion by a drive unit. To increase the abrasive effect, the instrument can be coated with additional particles as grinding powder, for example. Considering, however, that the instrument has a width and thickness of several millimeters, this device is not suited for cleaning interproximal spaces.

It is an object of the present invention to provide a dental cleansing device and a cleansing implement for an electrically powered dental cleansing device which enables in particular the interproximal spaces to be cleaned, which affords simple and secure manipulation, and which can be introduced into the interproximal spaces with particular ease.

According to the present invention, this object is essentially accomplished in that the cleansing implement is configured as an integrally formed part comprising a thin, elongate cleansing shaft which is flexible.

On account of the thin and elongate configuration of the cleansing shaft, the cleansing implement is also suitable for cleaning narrow interproximal spaces. Because the flexible cleansing shaft is adapted to be rotated about its longitudinal axis, it will automatically engage within the interproximal spaces. In the cleansing implement of the present invention, this automatic engaging action largely eliminates the possibility of injury otherwise occurring, for example, by improper manual insertion of dental floss into tight interdental spaces for lack of knowledge or experience of its user. Because the complete cleansing implement is formed as an integral part, economy of manufacture is achieved.

In a feature of the present invention, the cleansing shaft includes at least one longitudinal edge. In use of the cleansing implement, this longitudinal edge wipes off plaque from the user's teeth.

According to a further feature of the present invention, the cleansing shaft has an essentially square cross-section. As a result, the four longitudinal edges thus provided on the cleansing shaft make it possible to achieve an improved cleaning effect.

Advantageously, the sides of the cleansing shaft of essentially square cross-section have a length of 0.3 mm, approximately.

In a further feature of the present invention, a plurality of serrations project from the surface of the cleansing shaft. When the cleansing implement is in use, these serrations serve the function of removing plaque from the user's teeth.

It will be understood that the cleansing shaft may also be provided with stiffening ribs on its longitudinal sides which act as cleaning edges.

The cleansing shaft has preferably a length of between 10 and 15 mm. The thickness of the cleansing shaft is preferably in the range from 0.1 to 0.5 mm. The height and width of the serrations are preferably within the range of 0.1 and 0.3 mm.

In an advantageous further feature of the present invention, the cleansing implement is made of a plastics material. This allows economy of manufacture of the cleansing implement.

By providing the cleansing shaft with an unbalance by designed accumulation of material, the cleansing shaft is deflected from its rest position in the manner of a whip during rotation, which has a highly beneficial effect on the cleaning of the interproximal spaces.

In a still further feature of the present invention, the cleansing implement is adapted to be a push-fit on the dental cleansing device. This enables the user to substitute a new cleansing implement of like construction for a worn cleansing implement with ease and speed.

In an extremely advantageous feature, the cleansing implement is made of polyester elastomer or a material exhibiting like or similar properties. owing to the special properties of this material, the shaft of the cleansing implement can be bent by an angle of up to 180 degrees particularly also during use, without the risk of shaft rupture. For one thing, this practically precludes the possibility of injury by a ruptured shaft, and for another thing, it enables the teeth to be cleaned also in the subgingival region even when the shaft is bent by 180 degrees, in which event the cleaning function is mainly performed by the bent area of the bent shaft. Utilizing this material for the cleansing implement or also for the shaft itself results in improved manipulation also for the inexperienced user, in addition to enhancing the cleaning effect.

The present invention also relates to an electrically powered dental cleansing device in which an elongate, thin and flexible cleansing implement is adapted to be coupled to a drive shaft received in a handle section and is rotatable about its longitudinal axis.

Simple and secure manipulation of the dental cleansing device is essentially ensured in that in the dental cleansing device incorporating the features initially referred to an attachment is adapted to be push-fitted to the handle section, and that the cleansing implement is slidably received in the attachment.

By slidably accommodating the cleansing implement in the attachment, the possibility is provided to optimally adapt the dental cleansing device for its individual uses. Thus, the cleansing implement is slidable out of the attachment when a user desires to use the dental cleansing device for interproximal cleaning. By contrast, when the dental cleansing device is not in use, the cleansing implement can be pushed back into the interior of the attachment, thereby obviating the possibility of contamination of, or damage to, the cleansing implement. The cleansing implement thus also meets hygienic demands, in addition to being usable for a prolonged period. For example, when it is desired to take the cleansing implement on trips, it is ensured that the cleansing implement is not contaminated or damaged by other objects or, conversely, that the cleansing implement does not contaminate or damage these objects. When the cleansing implement is worn after prolonged use, the attachment with the cleansing implement therein received can be pulled off the handle section, and a new attachment with a new cleansing implement can be substituted. During such replacement, the user has no contact with the cleansing implement itself, but rather, can simply exchange it together with the attachment. However, the possibility may also be provided to push the attachment onto the handle section separate from the cleansing implement, requiring only the cleansing implement itself to be exchanged following use or wear.

In a feature of the present invention, the attachment has at the end remote from the handle section a guide tube in which the free end of the cleansing implement remote from the handle section is guided. When the cleansing implement is in the extended position relative to the attachment, the cleansing implement is located in position by the guide tube. This thus reliably prevents slippage or any other variation of the position of the cleansing implement during use.

In this arrangement, it will be advantageous to provide the guide tube with an approximately hemispherical rounded portion at its free end remote from the handle section, preferably with a diameter in the range from about 1 mm to about 4 mm, in particular about 2.5 mm. This rounded portion at the free end of the guide tube makes it easy for the user to probe the interproximal spaces, the rounded portion, when engaging against the teeth, being readily locatable centrally in the recesses existing in the region of the interproximal spaces. The * user, upon positioning the guide tube in the region of an interproximal space in this manner, may then slide the cleansing implement out of the attachment, inserting it in the interproximal space. Advantageously, the guide tube extends with its other end to the conical surface of the handle section, so that all parts coming into contact with the oral cavity are interchangeable if so desired, making the device suitable for use by several users, for example.

In a further feature of the present invention, the guide tube includes a bent portion, with the bending angle being in the range from about 30 degrees to about 150 degrees, in particular about 90 degrees. This facilitates the manipulation of the dental cleansing device as the user probes the interproximal spaces and introduces the cleansing implement therein for subsequently performing the cleaning operation.

In another feature of the present invention, the attachment is provided with means for releasably locating the cleansing implement in a transit position in which the cleansing implement is completely received within the attachment. In this transit position, the attachment with the cleansing implement therein received can be handled independently of the handle section and offered for sale, for example. Securing the cleansing implement in the transit position prevents the cleansing implement from accidentally slipping within the attachment and being damaged in the process.

It will be advantageous in this arrangement to provide the attachment with a sleeve-shaped portion having an inwardly projecting annular collar, and to provide the cleansing implement, at its end close to the handle section, with a disk-shaped base which includes an annular groove operatively associated with the annular collar and adapted for locking engagement with the annular collar to provide the transit position. By means of the annular collar and the annular groove, the cleansing implement is securely located in the transit position at low constructional expenditure.

In an extremely advantageous independent further feature of the present invention, the cleansing implement has at its end close to the handle section means for providing a releasable coupling to a drive shaft in a non-rotating relationship thereto, the drive shaft being adapted to be driven by a motor housed in the handle section. In this manner, the cleansing implement can be caused to rotate about its longitudinal axis. However, the non-rotative coupling does not connect the cleansing implement with the drive shaft inseparably, but rather, the cleansing implement can be pulled off the drive shaft. As a result, the attachment with the cleansing implement received therein is fully functional in pushedon condition without further means, and it can be pulled off the handle section and replaced as a whole, for example.

It will be an advantage in this arrangement to provide the cleansing implement and the drive shaft with a pin and an associated bore forming in assembled condition a press fit or having relatively associated complementary cross-sections. Such a simple structural approach provides the non-rotative coupling between the cleansing implement and the drive shaft.

In an advantageous feature of the present invention, the drive shaft is coupled to a longitudinally slidable switch for energizing and deenergizing the motor, such that a displacement of the switch also involves a displacement of the drive shaft in the longitudinal direction, whilst, however, rotation of the drive shaft is independent of the position of the switch. Accordingly, when the user moves the switch from the off-position to the on-position, this has at the same time the effect of displacing the drive shaft in the longitudinal direction. Because the cleansing implement is coupled to the drive shaft, also the cleansing implement will be displaced in the longitudinal direction. Thus, actuation of the switch will cause the cleansing implement to be extended from the attachment. Simultaneously with the extension of the cleansing implement from the attachment, the switch will also energize the motor, so that the cleansing implement, through its non-rotative coupling to the drive shaft, will be caused to rotate about its longitudinal axis. With the dental cleansing device in the activated position, the user can then clean the interproximal spaces using the extended and rotating cleansing implement. The attendant energization of the motor as the cleansing implement is extended from the attachment has the advantage of enabling the user to introduce the cleansing implement into the interproximal spaces to be cleaned with greater ease. This introduction will be still further supported by the threading effect produced by the rotating cleansing implement. When the user returns the switch to the off-position, this will have the effect of retracting the cleansing implement into the attachment and stopping its rotation.

It proves to be a great advantage that the switch for energizing the motor is slidable against a spring. As a result, the spring will automatically return the activated dental cleansing device to the off-condition should the user release the switch for whatever reason. This may occur, for instance, when the cleansing implement causes pain resulting from improper handling by its user. The spring will promptly act to deenergize the motor, pushing at the same time the cleansing implement back into the attachment. This protects the user from the possibility of pain or injury that may result from improper handling of the cleansing implement. The spring also ensures that the cleansing implement is outside the attachment only during the actual cleansing operation, being at all other times received inside the attachment in protected manner.

From a structural point of view it will be an advantage in this arrangement when, with the switch in the off-position, the drive shaft is in an inoperative position retracted relative to the attachment, in which position the cleansing implement coupled to the drive shaft is received inside the attachment. By contrast, with the switch in an on-position, the drive shaft is conveniently in an operative position extended relative to the attachment, in which position the cleansing implement coupled to the drive shaft is at least in part outside the attachment.

When in the operative position, it has proven to be particularly advantageous if a length in the range of about 8 mm to about 20 mm, in particular a length of about 12 mm, of the cleansing implement is outside the attachment. When the cleansing implement is pushed out of the attachment by about such a length, an optimum interproximal cleansing function can be performed.

In a further advantageous feature of the present invention, the motor fixedly accommodated in the handle section has a motor shaft with longitudinally extending vanes, and the drive shaft has at its end close to the motor a cup-shaped receptacle with longitudinal ribs in its interior, with the vanes of the motor shaft engaging longitudinally in the space between the longitudinal ribs of the cup-shaped receptacle in an overlapping fashion. As a result, the non-rotative connection between the motor shaft and the drive shaft is independent of the position of the drive shaft relative to the longitudinal direction. By means of the vanes and the longitudinal ribs, the rotary motion of the motor is thus transmitted from the motor shaft to the drive shaft. When the drive shaft is displaced in the longitudinal direction by means of the switch, the overlapping arrangement of the vanes and the longitudinal ribs in the longitudinal direction ensures continued interengagement of the vanes and the longitudinal ribs, so that transmission of the rotary motion from the motor shaft to the drive shaft is maintained at all events. The position of the switch and thus the position of the drive shaft in the longitudinal direction accordingly does not affect the non-rotative coupling of the motor shaft to the drive shaft.

According to an extremely advantageous, independent further aspect of the present invention, the attachment has at its end close to the handle section means for releasably locating the attachment in position on the handle section. In this manner, the attachment pushfitted to the handle section is securely held in place. When the user desires to separate the attachment from the handle section in order to replace, for example, a worn cleansing implement, this is still possible in a ready and simple manner.

In a feature of the present invention, the handle section and the attachment include at least one projecting lug and one associated recess which are in relative engagement with the attachment fitted. Conveniently, the lug is provided on the handle section, while the recess is provided on the inside of the attachment. It is, however, also possible to provide the lug on the attachment and the recess on the handle section. The lug and the recess ensure secure location of the attachment on the handle section at low constructional expenditure. By suitably flattening the lug in particular in the push-on and pull-off direction of the attachment, fitting and removing the attachment is further facilitated for its user.

Advantageously, the lug is associated with an opening extending through the attachment. This opening makes it easy for the user to check whether the lug is in proper locking engagement with the opening so that the attachment is completely fitted to the handle section.

In a further feature of the present invention, the attachment has at its end close the handle section means for aligning the attachment in a clearly defined position to the handle section in the circumferential direction. In this manner, the attachment, when fitted to the handle section, is located in a clearly defined position in the circumferential direction. Also, the possibility of the attachment turning on the handle section in the circumferential direction is prevented. Operation and manipulation of the dental cleansing device is thereby further facilitated and improved for the user.

In an advantageous feature of the present invention, the handle section and the attachment include at least one longitudinal ridge and one associated longitudinal groove which are in relative engagement with the attachment fitted. Conveniently, the longitudinal ridge is provided on the handle section, while the longitudinal groove is formed on the attachment. The reverse case is, however, also possible. The longitudinal ridge and the longitudinal groove afford simple constructional means for locating the attachment in a clearly defined position on the handle section in circumferential direction.

Still further, it will be an advantage to provide one longitudinal ridge and one longitudinal groove each on either side of the lug and recess, respectively. The arrangement of two longitudinal ridges and longitudinal grooves further facilitates the insertion of the attachment in the handle section for the user. The symmetrical arrangement of the longitudinal ridges and longitudinal grooves affords the further advantage of providing the dental cleansing device with a visually balanced appearance.

In still another feature of the present invention, three lugs and recesses, respectively, with associated longitudinal ridges and longitudinal grooves, respectively, are provided, which are arranged on the periphery of the handle section and, respectively, the attachment at partly non-uniform distances. As a result of this arrangement, the visual impression conveyed makes it easier for the user to properly fit the attachment to the handle section without further thinking. The location of the attachment on the handle section is thus visually expressed by the non-uniform arrangement.

Further features, advantages and application possibilities of the present invention will become apparent from the subsequent description of embodiments illustrated in more detail in the accompanying drawings. It will be understood that all features described and/or represented by illustration, whether taken alone or in any desired combination, constitute the subject-matter of the present invention, irrespective of their summarization in the claims and their back-references.

Figure 7:
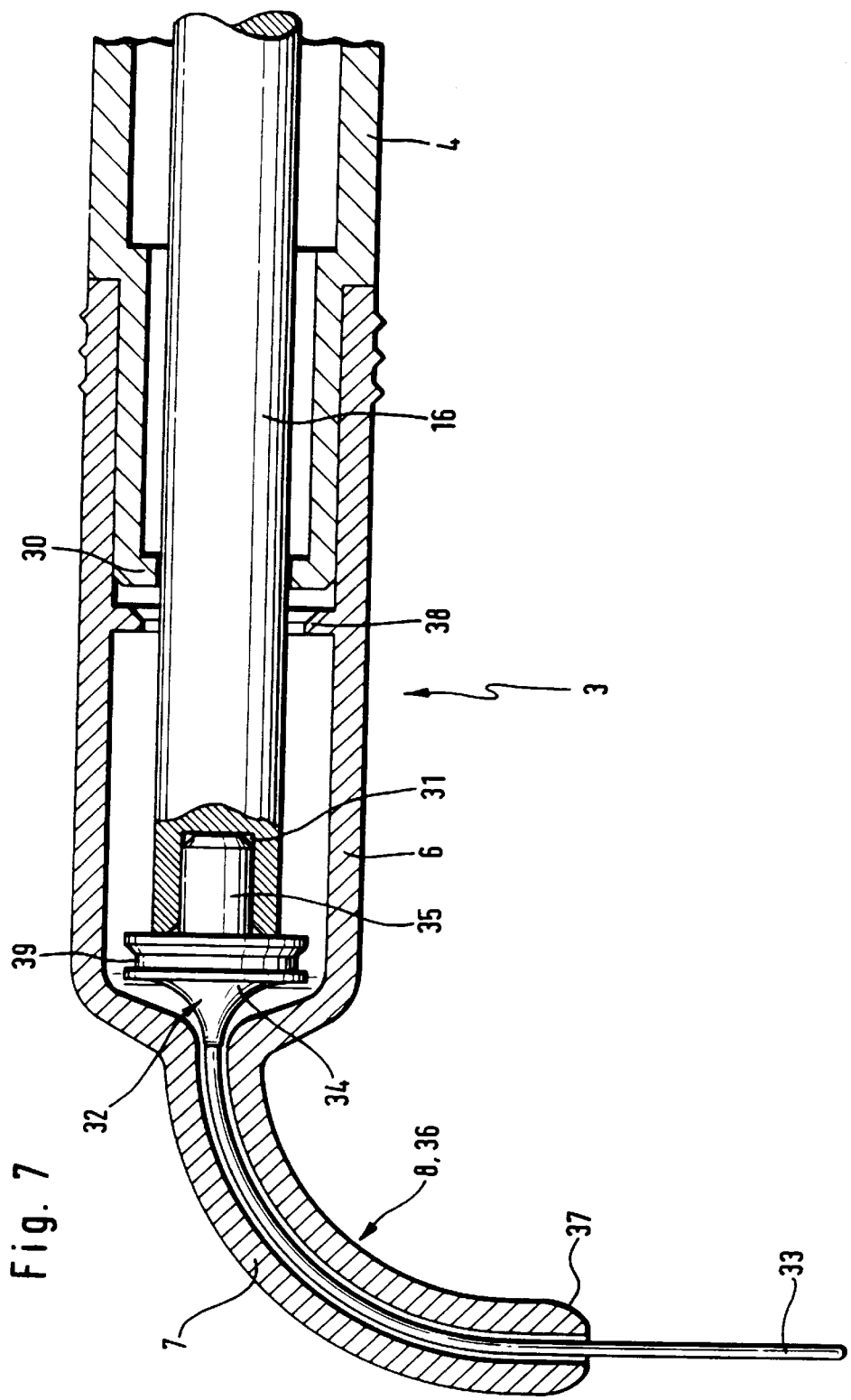
Figure 8:
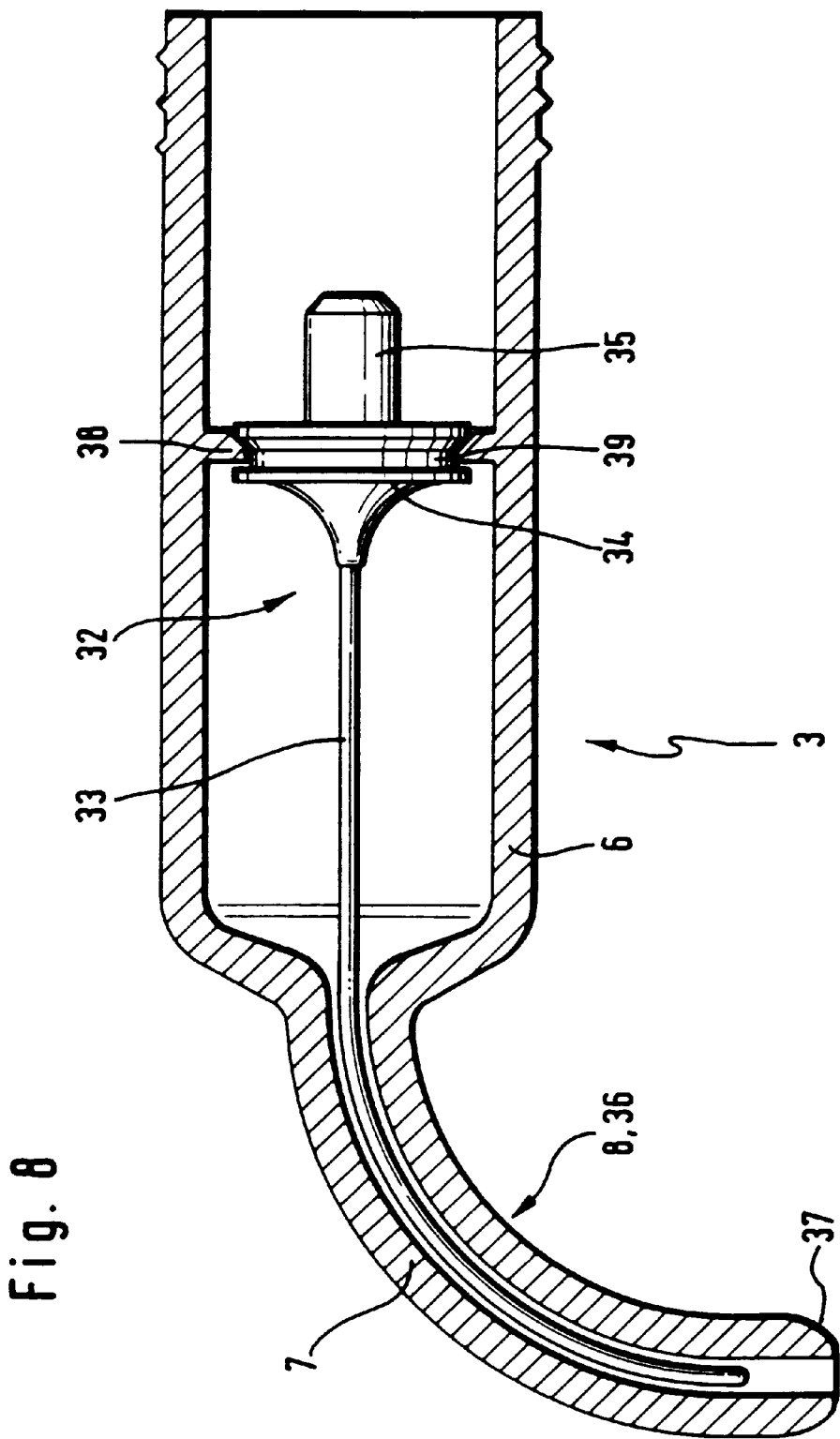
Figure 9:
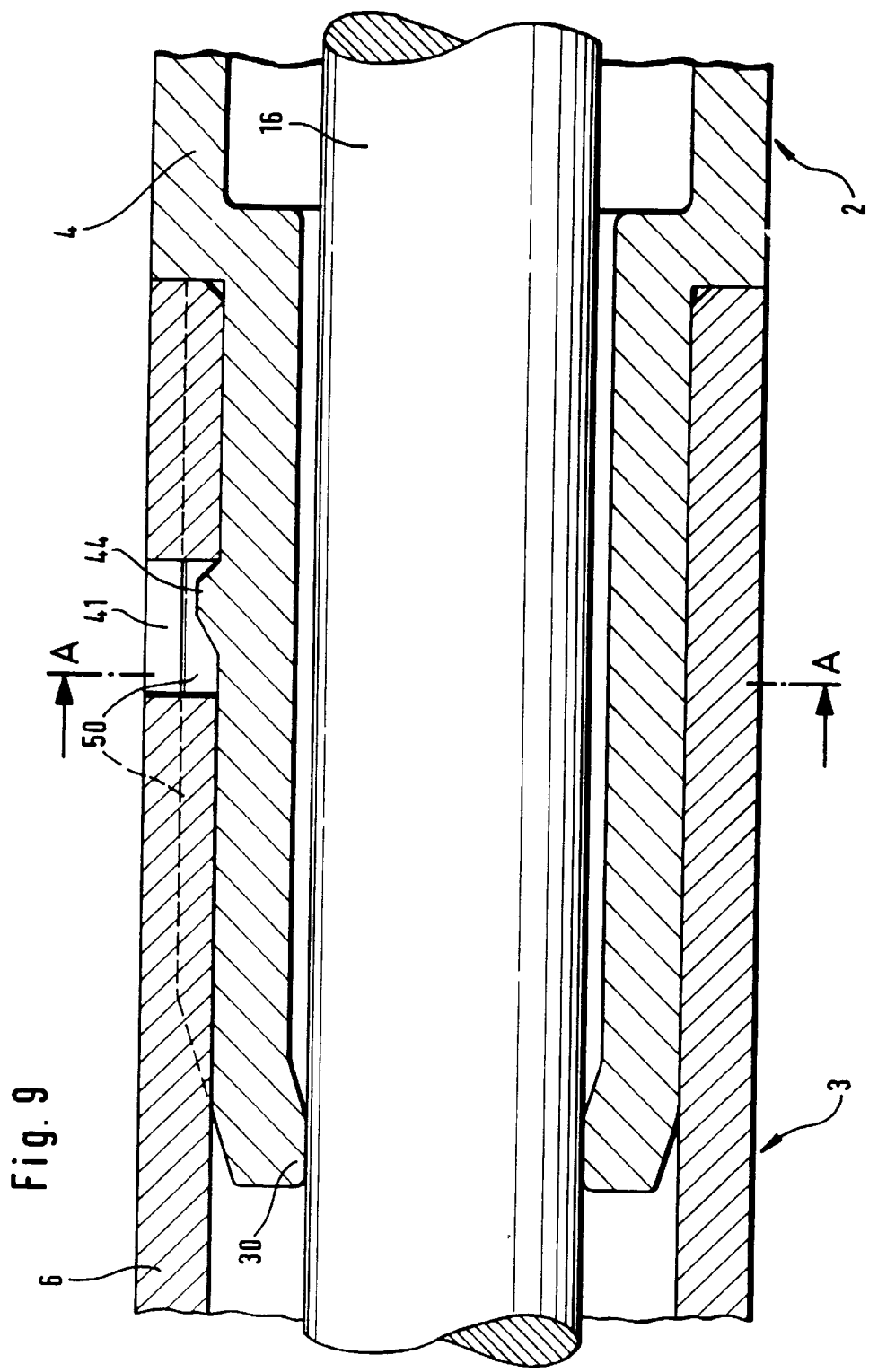
Figure 10:
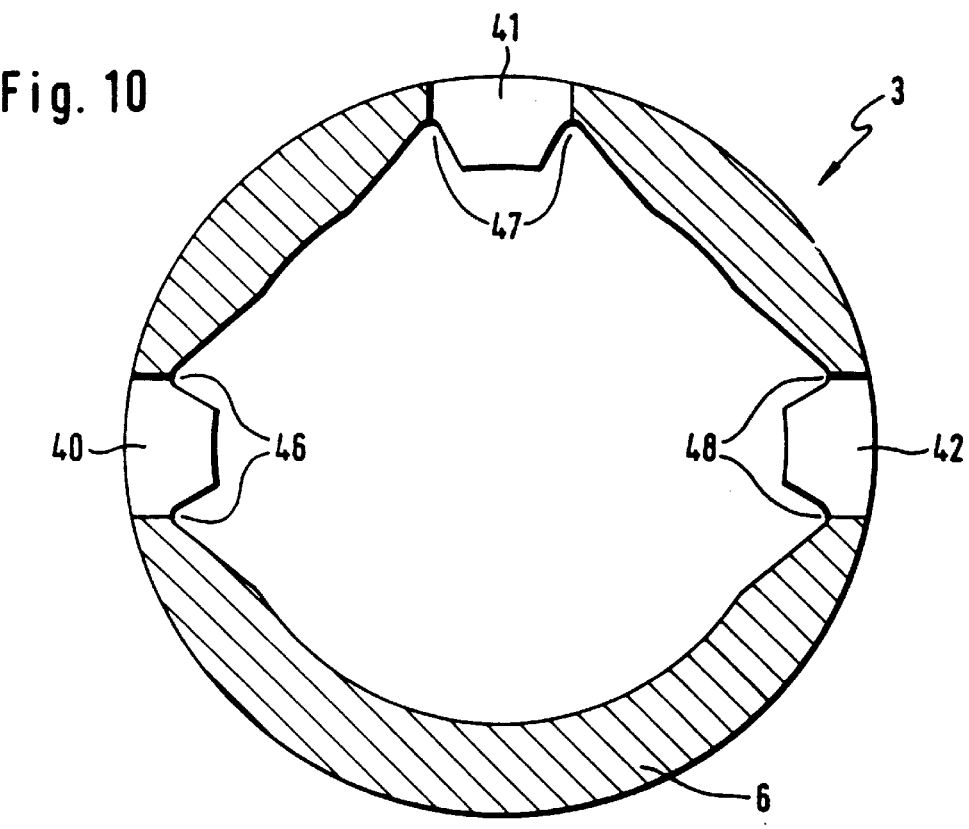
Figure 11:
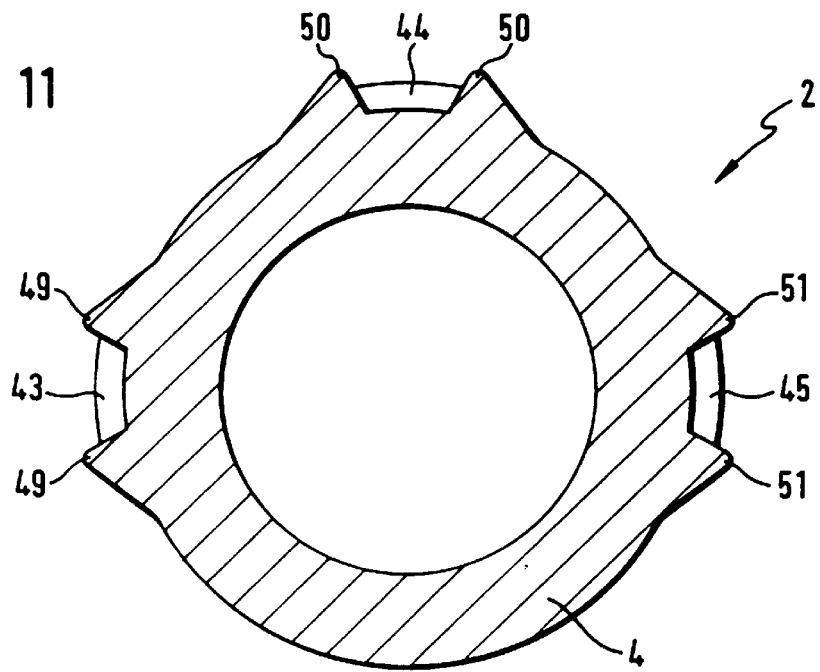

FIG. 7 a schematic view, partly in section and on an enlarged scale, of the attachment fitted to the handle section of the dental cleansing device in the operative position;

FIG. 8 is a schematic view, partly in section and on an enlarged scale, of the attachment in the transit position;

FIG. 9 is a schematic view, partly in section and on an enlarged scale, of the area in which the attachment is fitted to the handle section;

FIG. 10 is a schematic cross-sectional view of the attachment taken along the line A—A of FIG. 9; and FIG. 11 is a schematic cross-sectional view of the handle section taken along the line A—A of FIG. 9.

Figure 1:
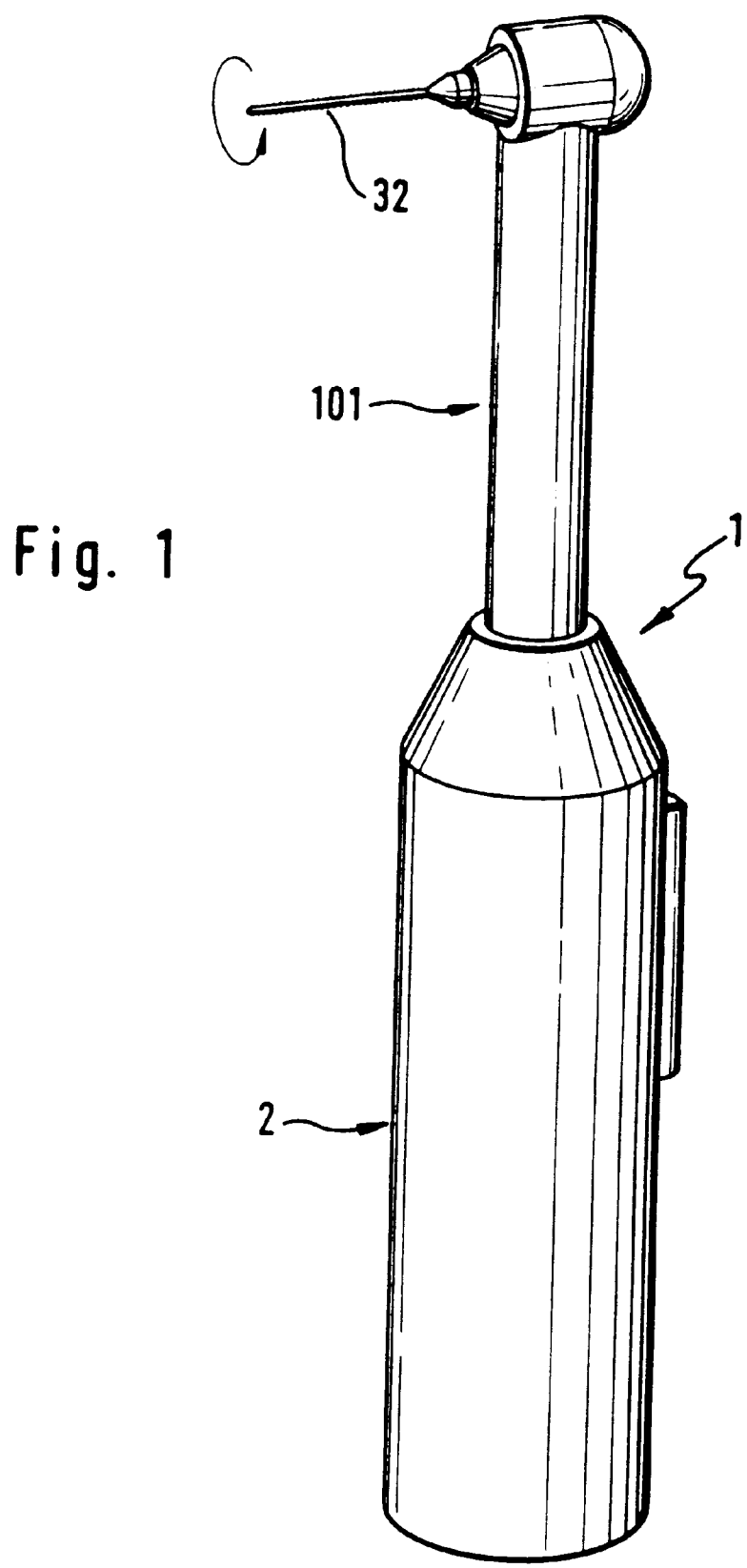
FIG. 1 is a perspective view of a dental cleansing device showing the cleansing implement in attached condition.

FIG. 1 shows a dental cleansing device 1 with a cleansing implement 32 attached. The dental cleansing device 1 includes a handle section 2 receiving an electric motor drive means adapted to be turned on and off by the user. Adjoining the handle section 2 is a mounting section 101 serving the function of transmitting and, where applicable, converting, the rotary motion produced by the electric motor drive means. The cleansing implement 32 is attachable to the head end of the mounting section 101. In FIG. 1, the cleansing implement 32 is arranged at the free end of the mounting section at an angle of about 90 degrees to the longitudinal axis of the mounting section 101 and the handle section 2. It is, however, also possible to arrange the cleansing implement 32 in the direction of the longitudinal axis of the mounting section 101 and the handle section 2 or to provide for adjustability between these positions. The cleansing implement 32 is attached to the free end of the mounting section 101 in such a manner as to be rotatable about its longitudinal axis by the electric motor drive means of the dental cleansing device 1. The rotational frequency may be about 3,000 1/min or higher, for example.

The cleansing implement 32 will be explained in greater detail in the following with reference to FIGS. 2 to 4.

Figure 2:
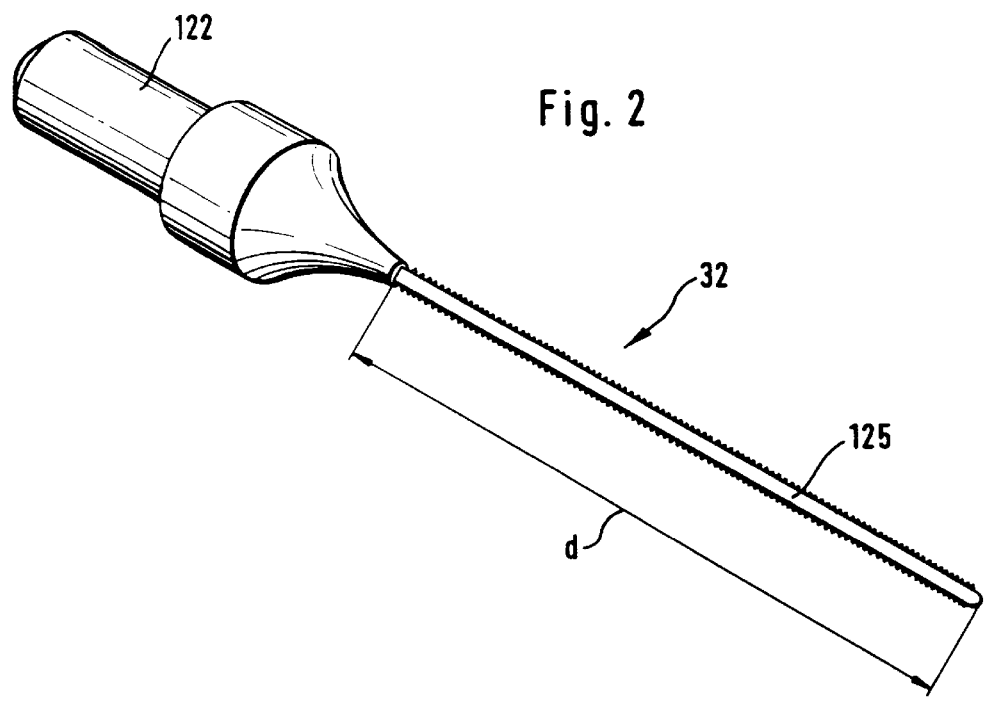
FIG. 2 is a view on an enlarged scale of the cleansing implement of FIG. 1.

The cleansing implement 32 of FIG. 2 is comprised of a mounting shaft 122 and a cleansing shaft 125, with the mounting shaft 122 with its diameter of about 1.5 mm being significantly thicker than the cleansing shaft 125 with a mean diameter of about 0.3 mm. By means of the mounting shaft 122 the cleansing implement 32 is attached to the free end of the mounting section 101 of the dental cleansing device 1. In FIG. 2, the mounting shaft 122 is of a cylindrical configuration, but it is also possible to provide the mounting shaft 122 with a different cross-sectional area, or to provide the mounting shaft 122 with additional longitudinal grooves or longitudinal ribs for non-rotative connection of the cleansing implement 32 with the electric motor drive means of the dental cleansing device 1. Through a transition area, the cleansing shaft 125 is connected with the mounting shaft 122 and serves to clean the teeth. The cleansing shaft 125 of FIG. 2 has a length d of about 12 mm and a thickness of between 0.3 and 0.4 mm±0.1 mm, which is thus substantially smaller than its length.

Figure 3:
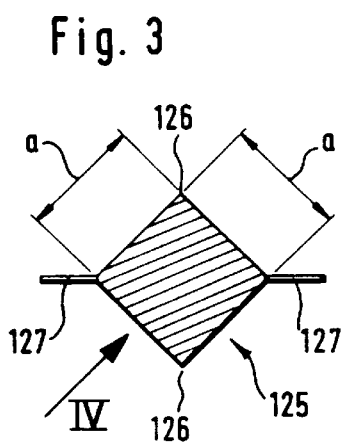
FIG. 3 is a cross-sectional view of the cleansing implement of FIG. 2, taken along the line III of FIG. 4.

As becomes apparent from FIG. 3, the cleansing shaft 125 has a square cross-sectional area. The four corners of this square cross-sectional area form longitudinal edges 126 extending substantially along the full length d of the cleansing shaft 125. The cross-sectional length a of the square cross-section is about 0.3 mm.

Figure 4:
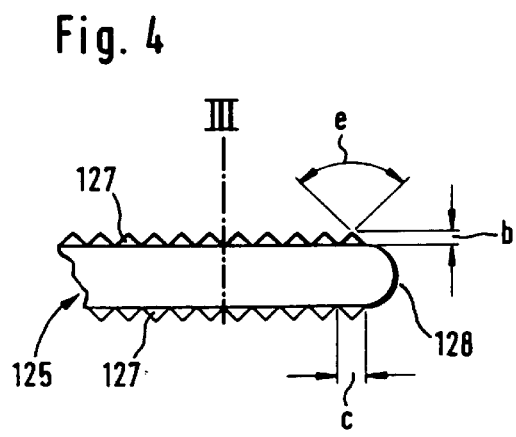
FIG. 4 is a side view of the cleansing implement of FIG. 2, as seen looking from the direction IV of FIG. 3.

A plurality of projecting serrations 127 are provided on the surface of the cleansing shaft 125, that is, on the surface bounded by the longitudinal edges 126, as illustrated schematically in FIG. 4. The height b of these serrations 127 is about 0.2 mm. The width c of a tooth 127 thereof is equally about 0.2 mm. Starting from a broad base on the surface of the cleansing shaft 125, the serrations 127 are tapered towards a pointed end. The taper angle e of the serrations 127 is about 90 degrees.

One end of the cleansing shaft 125 is advantageously provided with an essentially blunt, rounded portion 128 whose radius may be 0.2 mm, for example. This facilitates insertion of the cleansing implement into the interproximal spaces.

The complete cleansing implement 32 comprised of mounting shaft 122 and cleansing shaft 125 is configured as an integral component made of a plastics material and suitable for manufacture by injection molding. It will be particularly advantageous to use a plastic fiber with properties similar to that of dental floss. Further, greater ease of manufacture of the cleansing implement 32 is obtained by using a plastics material with good flow properties.

In use of the cleansing implement 32, it is particularly by means of the longitudinal edges 126 that plaque is wiped of f the teeth. The serrations 127 serve to loosen the plaque bacteria from the teeth. It will be understood that the cleansing implement 32 is also suitable for removing food particles from the teeth. The thin and elongate configuration of the cleansing implement 32 also enables tight interproximal spaces to be cleaned.

Because of the high rotational frequency of the cleansing implement 32 of about 3,000 1/min or higher, the flexible cleansing shaft 125 threads itself automatically into the interproximal spaces to be cleaned, also in cases where the user fails to position the dental cleansing device 1 accurately, which is a frequent occurrence particularly at inaccessible locations of a person's teeth. Moreover, the high rotational frequency of the cleansing implement 32 provides for rapid and thorough removal of plaque, being thus superior to conventional interproximal cleaning instruments as, for example, hand-operated toothpicks.

The cleansing shaft 125 or the complete cleansing implement 32 is preferably made of polyester elastomer, enabling the cleansing shaft 125 to be bent also during use by an angle of up to 180 degrees while rotating at a frequency of about 3,000 1/min±2,000 1/min.

Figure 5:
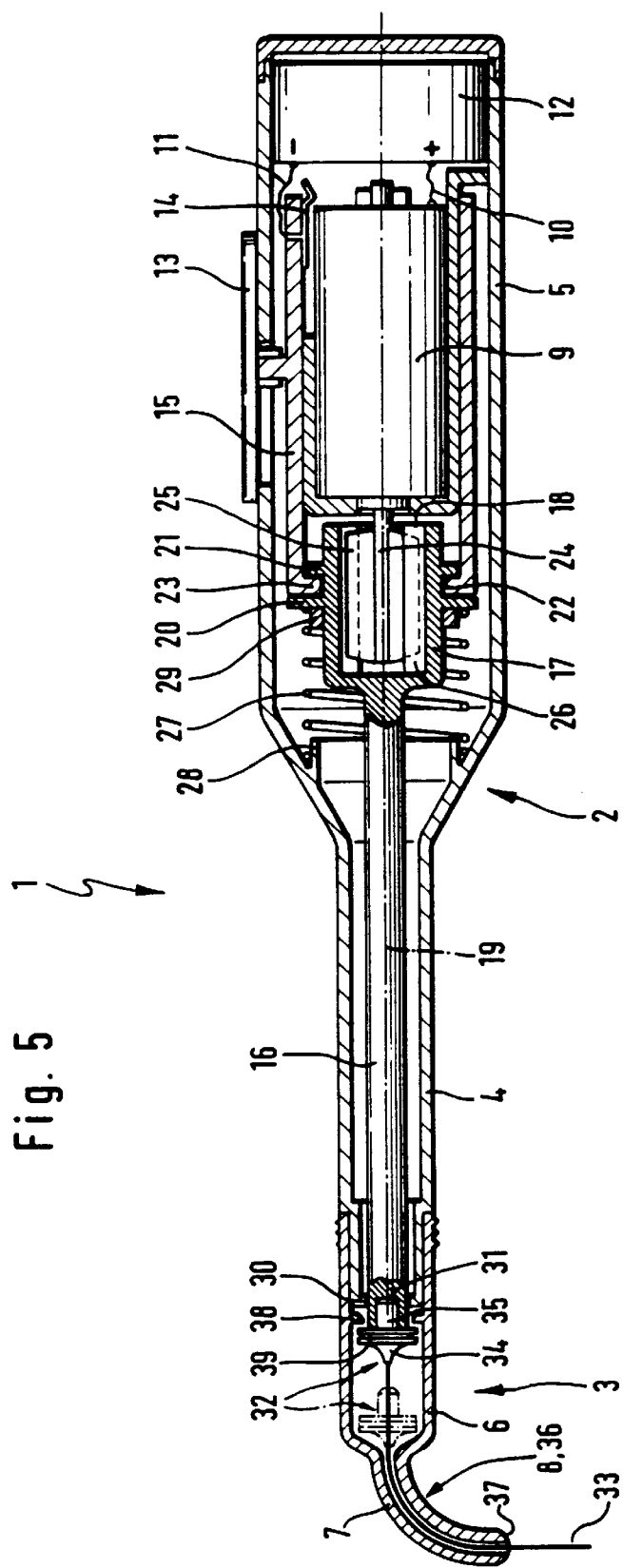
FIG. 5 is a schematic side view, partly in section, of an embodiment of a dental cleansing device of the present invention.

FIG. 5 shows a dental cleansing device 1 which is composed of a handle section 2 and an attachment 3 fitted thereto. The handle section 2 is of an elongate configuration with a circular cross-section. A portion 4 of the handle section 2 at the end close to the attachment 3 is of a reduced diameter compared to a portion 5 of the handle section 2 at the end remote from the attachment 3. The attachment 3 is equally of an essentially elongate configuration with a circular cross-section. The diameter of a portion 6 of the attachment 3 at the end close to the handle section 2 corresponds to the diameter of the portion 4 of the handle section 2. At the end remote from the handle section 2, the attachment 3 is provided with a guide tube 7 of a reduced diameter which includes a bent portion 8.

Fixedly mounted in the portion 5 of the handle section 2 is an electrically powered motor 9 connected to a voltage source 12, in particular a rechargeable accumulator, via an electric conductor 10. A longitudinally slidable switch 13 is equally housed in the portion 5 of the handle section 2. Provided on the switch 13 is an electrically conductive contact means 14 which in turn is e connected to the voltage source 12 via an electric conductor 11. The switch 13 further includes a coupling member 15 serving to couple the switch 13 to a drive shaft 16.

The drive shaft 16 extends through the entire portion 4 into the portion 5 of the handle section 2 and has at its free end close to the motor 9 in the area of the handle section 2 a cup-shaped receptacle 17 with an opening 18. The motor 9, the drive shaft 16 and the cup-shaped receptacle 17 are concentrically arranged with a common axis 19, with the opening 18 of the cup-shaped receptacle 17 being provided at the end close to the motor 9.

Projecting outwardly from the radial outside of the cup-shaped receptacle 17 are two relatively spaced annular collars 20, 21 defining an annular groove 22 therebetween for engagement by an annular collar 23 projecting inwardly from the coupling member 15. In this arrangement, the annular collar 23 engages with the annular groove 22 in such a manner that a displacement of the switch 13 in the longitudinal direction results at the same time in a displacement of the cup-shaped receptacle 17 likewise in the longitudinal direction. While the annular collar 23 is stationary in the circumferential direction, the cup-shaped receptacle 17 with its annular groove 22 is rotatable about the annular collar 23. The cup-shaped receptacle 17 is thus capable of rotating about the axis 19 irrespective of the position of the switch 13. It will be understood that a bearing or the like, not shown, may be arranged additionally in the area of the annular collar 23 and the associated annular groove 22, by means of which friction between the annular collar 23 and the annular groove 22 can be reduced, thereby facilitating the rotary motion of the cup-shaped receptacle 17 about the axis 19.

At the end of the cup-shaped receptacle 17 close to the opening 18, a motor shaft 24 extends from the motor 9, the shaft being arranged concentrically with the axis 19 as is the motor 9. The motor shaft 24 is provided with at least one, preferably however, three vanes 25 projecting radially outwardly from the motor shaft 24 and extending in the longitudinal direction. The cup-shaped receptacle 17 has in its interior a corresponding number of longitudinal ribs 26 projecting radially inwardly and extending likewise in the longitudinal direction. The vanes 25 extend through the opening 18 into the interior of the cup-shaped receptacle 17, engaging in the space between the longitudinal ribs 26. In this arrangement, the vanes 25 and the longitudinal ribs 26 overlap longitudinally along a length which is greater than the maximum length of displacement of the switch 13 in the longitudinal direction.

The vanes 25 and the longitudinal ribs 26 provide for transmission of the rotary motion of the motor shaft 24 to the cup-shaped receptacle 17 and thus to the drive shaft 16. The overlapping arrangement of the vanes 25 and the longitudinal ribs 26 in the longitudinal direction enables the cup-shaped receptacle 17 to be displaced by means of the switch, without the transmission of the rotary motion of the motor shaft 24 to the drive shaft 16 being affected thereby. It will be understood that this coupling structure between the motor shaft 24 and the drive shaft 16 by means of the vanes 25 and the longitudinal ribs 26 may also be configured in a different manner, providing, for example, a suitable gearing or the like.

Seated between the side of the annular collar 20 facing the portion 4 of the handle section 2 and the transition area between the portion 5 and the portion 4 of the handle section 2 is a spring 27 which is located in position by means of support walls 28, 29. The spring 27 produces a force acting in opposition to a displacement of the switch 13 towards the attachment 3. As a result, the spring 27 invariably urges the switch 13 and thus the drive shaft 16 automatically into a direction away from the attachment 3 without any external influence.

As described in the foregoing, the drive shaft 16 extends along the full length of the portion 4 of the handle section 2. At the end of the handle section 2 close to the attachment 3, the drive shaft 16 is guided by an annular collar 30 projecting inwardly from the handle section 2. Further, the drive shaft 16 projects at this end from the handle section 2 by a small amount, its free end being provided with a bore 31 extending concentrically with the axis 19.

In the attachment 3 fitted to the handle section 2, a cleansing implement 32 is longitudinally slidably received. The cleansing implement 32 includes a cleansing shaft 33 of an elongate and thin configuration. Preferably, the cleansing shaft 33 is about 30 mm long with a diameter of about 0.5 mm. The cleansing shaft 33 is made of a plastics material, in particular a polyester elastomer as, for example, HYTREL™. The cleansing shaft 33 is flexible, allowing bending by an angle of up to 150 degrees, minimum, also as it rotates about its longitudinal axis.

At its end close to the drive shaft 16, the cleansing implement 32 includes a circular base 34 connected to the cleansing shaft 33, as well as a pin 35 connected to the base 34. The pin 35 of the cleansing implement 32 is received in the bore 31 of the drive shaft 16. The pin 35 and the bore 31 may press-fitted together or, alternatively, the cross-sectional shapes of the pin 35 and the bore 31 may be conformed to each other, for example, in the form of a polygon or the like.

As set forth previously, the attachment 3 is fitted to the handle section 2. Further, the pin 35 is inserted in the bore 31 in a non-rotating relationship thereto. The cleansing shaft 33 extends from the base 34 to the guide tube 7 and is then passed through the guide tube 7.

Because of the bent portion 8 of the guide tube 7, the cleansing shaft 33 includes likewise a correspondingly bent portion 36. In the Figures, an angle of about 90 degrees is provided for the bent portions 8 and 36. It will be understood that the bent portions 8 and 36 may also be bent at different angles, particularly at angles in the range from about 30 degrees to about 150 degrees.

The free end of the guide tube 7 is provided with an essentially hemispherical rounded portion 37. The diameter of this rounded portion 37 amounts to a value in the range from about 1 mm to about 4 mm, in particular a value of about 2.5 mm.

The dental cleansing device 1 illustrated in FIG. 5 provides two modes, an off-mode in which the cleansing implement 32 is in the inoperative position, and an onmode in which the cleansing implement 32 is in the operative position. FIG. 5 shows the cleansing implement 32 in both the inoperative and the operative position, illustrating the base 34 and the pin 35 of the cleansing implement 32 twice, once for each position. However, the drive shaft 16 and the other parts of the dental cleansing device 1 are all shown in the off-mode and thus in their inoperative positions.

Figure 6:
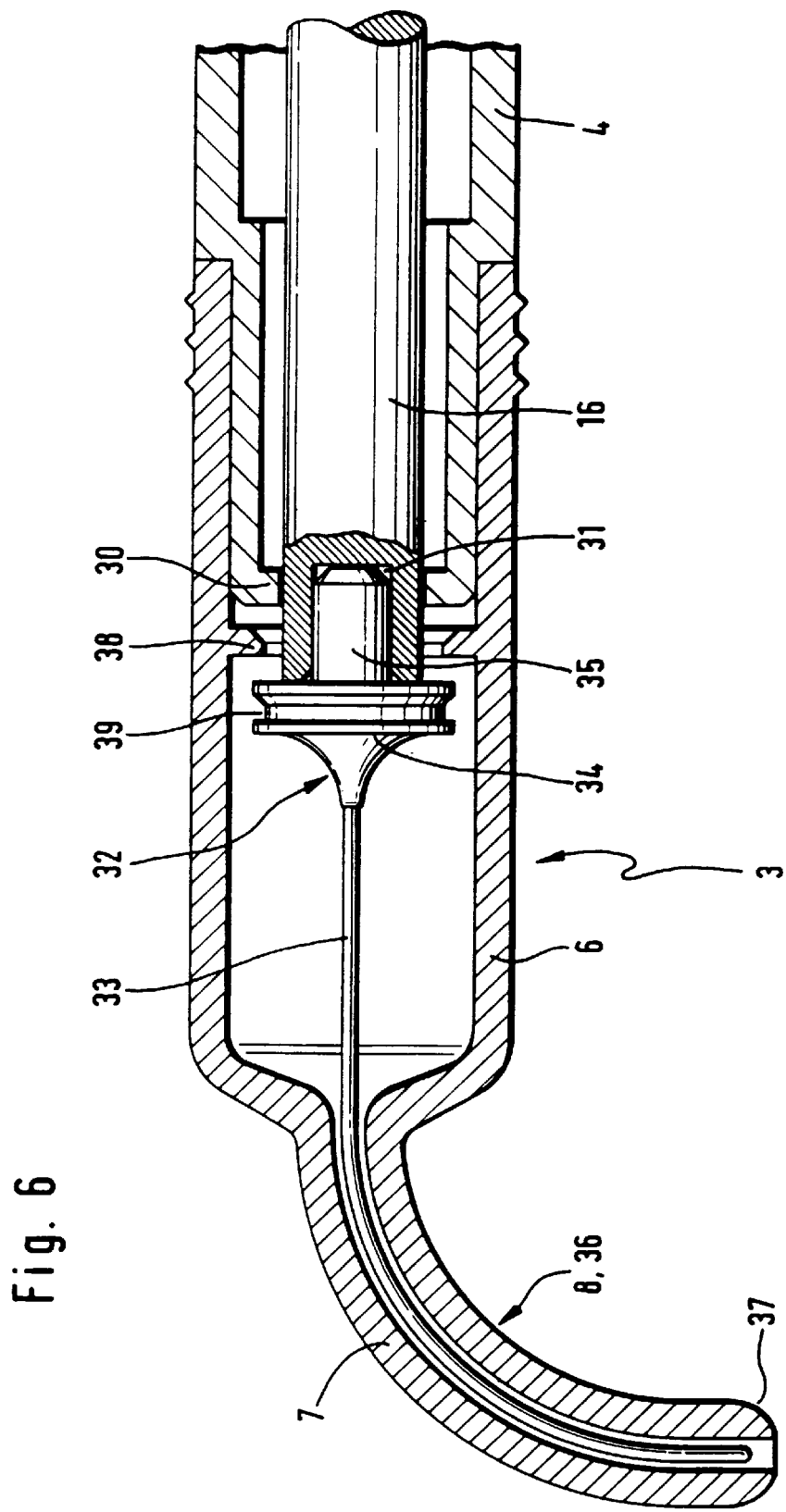
FIG. 6 is a schematic view, partly in section and on an enlarged scale, of the attachment fitted to the handle section of the dental cleansing device in the inoperative position.

FIGS. 6 and 7 are provided for a better understanding of the on and off-modes with the related operative and inoperative positions. FIG. 6 shows the cleansing implement 32 in the inoperative position, while FIG. 7 shows the operative position thereof. In the subsequent description, reference will be preferably made first to the two last-mentioned FIGS. 6 and 7, while for the explanation of the mode of function FIG. 5 will be referred to preferably.

In the inoperative position shown in FIG. 6, the cleansing implement 32 and in particular the cleansing shaft 33 are fully received in the interior of the attachment 3. The base 34 and the pin 35 are in the immediate proximity of the end of the handle section 2 close to the attachment 3. In contrast thereto, in the operative position shown in FIG. 7, the cleansing implement 32 is not fully received inside the attachment 3. The free end of the cleansing shaft 33 projects from the free end of the guide tube 7. Preferably, the cleansing shaft 33 projects from the guide tube 7 with a length of about 10 mm to about 15 mm, in particular about 12 mm. This is accomplished by longitudinal displacement of the base 34 and the pin 35 of the cleansing implement 32 away from the handle section 2. The base 34 and the pin 35 are then no longer in the proximity of the handle section 2, but rather, approximately in the transition area between the portion 6 of the attachment 3 and the guide tube 7. The base 34 and the pin 35 are displaced within the attachment 3 by a length corresponding precisely to the amount by which the cleansing shaft 33 projects from the guide tube 7.

In the inoperative position the switch 13 is in its off-position as shown in FIG. 5. The contact means 14 is not in electrical contact with the electrically conductive surface of the motor 9. The motor 9 is accordingly off. The motor shaft 24 and thus the drive shaft 16 and the cleansing implement 32 do not rotate. Due to the position of the switch 13 and the force exerted by the spring 27 on the cup-shaped receptacle 17, also the drive shaft 16 is in the inoperative position illustrated in FIG. 5. As a result, the retracted position of the drive shaft 16 towards the motor 9 also causes the cleansing implement 32 to be in its inoperative position illustrated in FIG. 6, in which in particular the cleansing shaft is fully received in the interior of the attachment 3.

When a user then shifts the switch 13 in the longitudinal direction towards the attachment 3, the contact means 14 will contact the electrically conductive surface of the motor 9. The circuit for energization of the motor 9 will thereby be closed via the conductor 10, the voltage source 12, the contact means 14, and the conductor 11. The motor shaft 24 will thus be caused to rotate about the axis 19. By means of the vanes 25 and the longitudinal ribs 26, this rotary motion will be transmitted to the drive shaft 16. Via the bore 31 and the pin 35, the rotary motion will then be transmitted to the cleansing implement 32, causing the cleansing shaft 33 to rotate about its own axis partly rectilinearly and partly along its bent portion 36.

Displacement of the switch 13 by the user results at the same time in a displacement of the drive shaft 16 in the same direction through the annular collar 23 and the annular groove 22. This motion is transmitted to the cleansing implement 32 via the bore 31 and the pin 35. As a result, the cleansing shaft 33 moves from its inoperative position away from the handle section 2 in the direction of its operative position illustrated in FIG. 7. When the switch 13 has completed its displacement travel to its maximum permissible on-position, the amount of extension of the cleansing shaft from the guide tube is at its maximum, as shown in FIG. 7. The rotating and fully extended cleansing shaft 33 then enables the user to clean the interproximal spaces.

When the user releases the switch 13, it will be shifted back to its off-position by the force of the spring 27. This will also cause the cleansing implement 32 to return to its inoperative position. At the same time, the contact means 14 will stop contacting the motor 9, causing the motor 9 to be off. The dental cleansing device 1 is again in the off-condition previously explained.

FIG. 8 shows the attachment 3 with the cleansing implement 32 received therein as a separate part, that is, detached from the handle section 2. The attachment 3 has about centrally in its portion 6 an inwardly projecting annular collar 38. Further, the circular base 34 of the cleansing implement 32 is provided with an annular groove 39 conformed to the annular collar 38. In the transit position of the cleansing implement 32 shown in FIG. 8, the annular groove 39 is in locking engagement with the annular collar 38. This securely captures the cleansing implement 32 inside the attachment 3. The annular collar 38 and the annular groove 39 are arranged such that in the transit position described the cleansing implement 32 is fully received within the attachment 3.

When the attachment 3, with the cleansing implement 32 in locking engagement therewith, is fitted to the handle section 2, this has the attendant effect of inserting the pin 35 into the bore 31. Shortly before the attachment 3 is completely push-fitted to the handle section 2, the annular collar 38 will be disengaged from the annular groove 39, so that the cleansing implement 32, rather than being held captive inside the attachment 3, will then be coupled to the drive shaft 16 through the pin 35 and the bore 31.

When the attachment 3 is withdrawn from the handle section 2, the base 34 will abut the annular collar 38, causing the pin 35 of the cleansing implement 32 to be pulled out of the bore 31. The cleansing implement 32 will not remain coupled to the drive shaft 16, but rather, it will be pulled off together with the attachment 3.

Referring to FIGS. 9 to 11, it will now be explained how the attachment 3 is fitted to the handle section 2. As shown, the attachment 3 includes three openings 40, 41 and 42 spaced at an angle of about 90 degrees on the periphery of the attachment 3. In the absence of a fourth opening, the three openings 40, 41 and 42 provided are partly non-uniformly spaced on the periphery of the attachment 3. Each of the openings 40, 41 and 42 is associated with a respective lug 43, 44 and 45 projecting approximately radially outwardly from the handle section 2.

In the area of overlap with the handle section 2, the attachment 3 has an increased diameter to enable the lugs 43, 44 and 45 of the handle section 2 to engage the respective openings 40, 41 and 42 of the attachment 3. This is illustrated in FIG. 9. The lugs 43, 44 and 45 are of a flattened configuration in the longitudinal direction, thus enabling the user to insert and withdraw the handle section 2 in and from the attachment 3 without major effort. In the locked condition illustrated in FIG. 9, the lugs 43, 44 and 45 engaging the respective openings 40, 41 and 42 are visible to the eye.

As appears particularly from FIG. 10 showing a cross-sectional view of the attachment 3, each of the openings 40, 41 and 42 is associated with a respective pair of longitudinal grooves 46, 47 and 48. Correspondingly, each of the lugs 43, 44 and 45 is associated with a respective pair of longitudinal ridges 49, 50, 51, as becomes apparent particularly from FIG. 11 showing a cross-sectional view of the handle section 2. When viewed in the circumferential direction, one longitudinal groove is provided on either side of the openings 40, 41 and 42, and one longitudinal ridge is provided on either side of the lugs 43, 44 and 45. The longitudinal grooves 46, 47 and 48 and the longitudinal ridges 49, 50 and 51 are conformed to each other such as to be in relative engagement when the attachment 3 is fitted to the handle section 2, the longitudinal ridges 49, 50 and 51 then sliding along inside the longitudinal grooves 46, 47 and 48.

By means of in particular the longitudinal grooves 46, 47 and 48 and the longitudinal ridges 49, 50 and 51, the attachment 3 is located in a clearly defined position on the handle section 2 in the circumferential direction. Obviously, not all of the longitudinal ridges, longitudinal grooves, openings and lugs may be necessary for such a location. In the simplest case, a single lug will suffice which engages an associated through opening or a non through-going recess, thereby locating the attachment 3 in a clearly defined position on the handle section 2 in the circumferential direction. Equally obviously, such a location can also be accomplished by means of other structural arrangements.

What is claimed is:

1. An electrically powered dental cleansing device comprising:
   a handle section having a drive shaft received therein;
   a cleansing implement configured to be coupled to the drive shaft and to be set in rotation by the drive shaft about its longitudinal axis; and
   an attachment, wherein the cleansing implement is slidably and rotatably received in the attachment which is adapted to be push-fitted to the handle section.

2. The electrically powered dental cleansing device as claimed in claim 1, wherein the attachment includes at an end remote from the handle section a guide tube in which a free end of the cleansing implement remote from the handle section is guided.

3. The electrically powered dental cleansing device as claimed in claim 2, wherein the guide tube is provided with an approximately hemispherical rounded portion at its free end remote from the handle section, with a diameter in the range from about 1 mm to about 4 mm.

4. The electrically powered dental cleansing device as claimed in claim 2, wherein the guide tube is provided with an approximately hemispherical rounded portion at its free end remote from the handle section, with a diameter of about 2.5 mm.

5. The electrically powered dental cleansing device as claimed in claim 2, wherein the guide tube of the attachment includes a bent portion, with a bending angle in the range from about 30 degrees to about 150 degrees.

6. The electrically powered dental cleansing device as claimed in claim 2, wherein the guide tube of the attachment includes a bent portion, with a bending angle of about 90 degrees.

7. The electrically powered dental cleansing device as claimed in claim 1, wherein the attachment includes an annular collar configured to releasably locate the cleansing implement in a transit position in which the cleansing implement is completely received within the attachment.

8. The electrically powered dental cleansing device as claimed in claim 1, wherein the attachment includes a sleeve-shaped portion having an inwardly projecting annular collar, and the cleansing implement, at its end closest to the handle section, includes a disk-shaped base having an annular groove operatively associated with the annular collar and adapted to lockingly engage with the annular collar to provide a transit position of the cleansing implement.

9. The electrically powered dental cleansing device as claimed in claim 1, wherein the cleansing implement includes at its end close to the handle section a pin configured to couple to the drive shaft in an non-rotating relationship thereto, said drive shaft configured to be driven by a motor housed in the handle section.

10. The electrically powered dental cleansing device as claimed in claim 1,
wherein the cleansing implement includes a pin and the drive shaft includes a bore,
said pin and said bore having relatively associated complementary cross-sections which in assembled condition form a press-fit.

11. The electrically powered dental cleansing device as claimed in claim 1, wherein the attachment includes at its end closest to the handle section at least one recess configured to releasably locate the attachment in position on the handle section.

12. The electrically powered dental cleansing device as claimed in claim 1, wherein the handle section and the attachment include at least one projecting lug and one associated recess which are in relative engagement with the attachment push-fitted onto the handle section.

13. The electrically powered dental cleansing device as claimed in claim 12, wherein the lug is associated with an opening extending through the attachment.

14. The electrically powered dental cleansing device as claimed in claim 11, wherein the attachment includes at its end closest to the handle section a longitudinal groove for aligning the attachment in a clearly defined position in the circumferential direction relative to the handle section.

15. The electrically powered dental cleansing device as claimed in claim 11, wherein the handle section and the attachment include at least one longitudinal ridge and one associated longitudinal groove which are in relative engagement with the attachment push-fitted onto the handle section.

16. The electrically powered dental cleansing device as claimed in claim 15, wherein the handle section and the attachment include at least one projecting lug and one associated recess which are in relative engagement with the attachment push-fitted onto the handle section; and wherein one longitudinal ridge and one longitudinal groove each are provided on either side of the lug and the recess, respectively.

17. The electrically powered dental cleansing device as claimed in claim 16, wherein the handle section and the attachment include three lugs and recesses, respectively, with associated longitudinal ridges and longitudinal grooves, respectively, arranged with at least partly non-uniform distances on the periphery of the handle section and, respectively, of the attachment.

18. The electrically powered dental cleansing device as claimed in claim 1, wherein the cleansing implement is an integrally formed part, including a cleansing shaft which is flexible and made of a polyester elastomer or a material of similar flexural strength, and can be set in rotation by a motor of the dental cleansing device.

19. The electrically powered dental cleansing device as claimed in claim 18, wherein the cleansing shaft includes at least one longitudinal edge.

20. The electrically powered dental cleansing device as claimed in claim 18, wherein the cleansing shaft has an essentially square cross-section.

21. The electrically powered dental cleansing device as claimed in claim 20, wherein a side of the square cross-section has a length of approximately 0.3 mm.

22. The electrically powered dental cleansing device as claimed in claim 18, wherein a plurality of serrations project from a surface of the cleansing shaft.

23. The electrically powered dental cleansing device as claimed in claim 22, wherein each serration has a height of approximately 0.2 mm.

24. The electrically powered dental cleansing device as claimed in claim 23, wherein each serration has a width of approximately 0.2 mm.

25. The electrically powered dental cleansing device as claimed in claim 18, wherein the cleansing shaft is integrally formed having an unbalanced structure.

26. The electrically powered dental cleansing device as claimed in claim 18, wherein the cleansing shaft has a length of 12 mm.

27. The electrically powered dental cleansing device as claimed in claim 18, wherein the cleansing implement is made of Hytrel®.

28. The electrically powered dental cleansing device as claimed in claim 18, wherein the cleansing implement is configured to be a push-fit on the dental cleansing device.

29. The electrically powered dental cleansing device as claimed in claim 18, wherein the cleansing shaft includes at one end a blunt rounded portion.

30. The electrically powered dental cleansing device as claimed in claim 18, wherein the cleansing shaft is thin and elongate.

31. An electrically powered dental cleansing device comprising:
a handle section including a drive shaft, a motor coupled to a drive shaft, and a switch to which the drive shaft is coupled and which is for energizing and de-energizing the motor, wherein a displacement of the switch also effects a displacement of the drive shaft in a longitudinal direction relative to the drive shaft;

a cleansing implement configured to be coupled to the drive shaft and to be set in rotation about its longitudinal axis; and an attachment in which the cleansing implement is slidably and rotatably received and which is adapted to be push-fitted to the handle section.

32. The electrically powered dental cleansing device of claim 31 wherein the switch is slidable in the longitudinal direction of the handle section.

33. The electrically powered dental cleansing device as claimed in claim 31, wherein the switch for energizing the motor is slidable against a spring.

34. The electrically powered dental cleansing device as claimed in claim 31, wherein in the off-position of the switch the drive shaft is in an inoperative position retracted relative to the attachment, in which position the cleansing implement connected to the drive shaft is received inside the attachment.

35. The electrically powered dental cleansing device as claimed in claim 31, wherein in an on-position of the switch the drive shaft is in an operative position extended relative to the attachment, in which position the cleansing implement connected to the drive shaft is at least in part outside the attachment.

36. The electrically powered dental cleansing device as claimed in claim 35, wherein a length in the range of about 8 mm to about 20 mm of the cleansing implement is outside the attachment.

37. The electrically powered dental cleansing device as claimed in claim 35, wherein a length of about 12 mm of the cleansing implement is outside the attachment.

38. The electrically powered dental cleansing device as claimed in claim 31, wherein the motor is fixedly accommodated in the handle section and includes a motor shaft having longitudinally extending vanes, and the drive shaft includes at its end closest to the motor a cup-shaped receptacle having longitudinal ribs in its interior, wherein the vanes of the motor shaft overlappingly and longitudinally engage the space between the longitudinal ribs of the cup-shaped receptacle.

* * * * *